(12) United States Patent
Ongaro

(10) Patent No.: US 7,214,354 B2
(45) Date of Patent: May 8, 2007

(54) AUTOCLAVE

(75) Inventor: Daniele Giovanni Ongaro, Villa di Serio (IT)

(73) Assignee: W & H Sterilization srl, Pedrengo (Bergamo) (IT)

( * ) Notice: Subject to any disclaimer, the term of this patent is extended or adjusted under 35 U.S.C. 154(b) by 435 days.

(21) Appl. No.: 10/170,147

(22) Filed: Jun. 12, 2002

(65) Prior Publication Data

US 2003/0007914 A1  Jan. 9, 2003

(30) Foreign Application Priority Data

Jul. 3, 2001  (AT) .............................. A 1032/2001

(51) Int. Cl.
*A61L 2/06* (2006.01)
(52) U.S. Cl. ..................... 422/298; 122/441; 95/257
(58) Field of Classification Search .............. 422/298; 210/126; 95/241, 257; 122/441
See application file for complete search history.

(56) References Cited

U.S. PATENT DOCUMENTS

| | | | | |
|---|---|---|---|---|
| 2,103,770 A | * | 12/1937 | Dunham et al. | 237/1 R |
| 2,215,517 A | * | 9/1940 | Van Vulpen et al. | 237/9 R |
| 2,267,941 A | * | 12/1941 | Miller | 122/441 |
| 2,430,837 A | * | 11/1947 | Tutein | 165/299 |
| 3,488,925 A | * | 1/1970 | Arbogast | 96/197 |
| 3,717,434 A | * | 2/1973 | Black | 422/112 |
| 3,934,799 A | * | 1/1976 | Hull | 237/67 |
| 4,613,071 A | * | 9/1986 | Omori | 237/9 R |

FOREIGN PATENT DOCUMENTS

EP  0 992 247 A1 *  4/2000

OTHER PUBLICATIONS

Dictionary definition of tight The American Heritage® Dictionary of the English Language, Fourth Edition Copyright © 2004, 2000 by Houghton Mifflin Company. Published by Houghton Mifflin Company.*

* cited by examiner

*Primary Examiner*—Krisanne Jastrzab
*Assistant Examiner*—Sean E. Conley
(74) *Attorney, Agent, or Firm*—Friedrich Kueffner

(57) ABSTRACT

The invention relates to an autoclave for medical appliances and instruments with a chamber (13) in which the appliances to be sterilized are located, with a steam generator (5) and a condensate collector (11), whereby the steam generator is connected with the chamber (13) by a steam pipe (9) and the condensate collector (11) is connected with the chamber (13) by a feed pipe (35) of the condensate.

Figure 1:
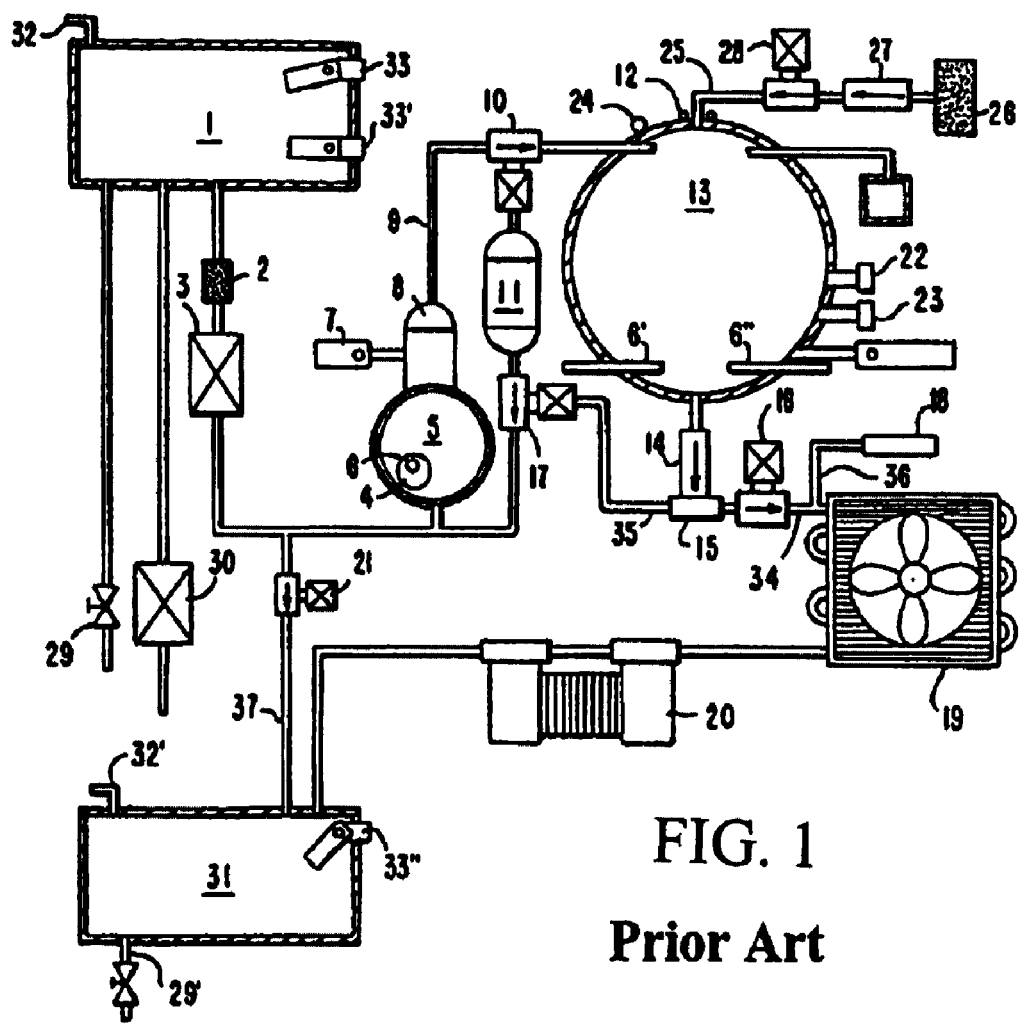

The invention is characterized in that the condensate collector (11) is positioned above the steam generator (5), staggered with respect to the steam generator (5), by positioning a check valve (41) between the condensate collector (11) and the steam generator (5) and by providing a check valve (39) at the mouth of the feed pipe (35) of the condensate to the condensate collector (11).

6 Claims, 2 Drawing Sheets

AUTOCLAVE

The invention relates to an autoclave for medical appliances and instruments with a chamber in which the appliances to be sterilised are located, with a steam generator and a condensate collector, whereby the steam generator is connected with the chamber by a steam pipe and the condensate collector is connected with the chamber by a feed pipe of the condensate Such an autoclave is known e.g. from the EP 0 992 247 A1. The design of such autoclaves has to be rather compact in order to use the space available in medical practices and consulting rooms of hospitals and outpatient clinics in the best possible manner. Furthermore, the time required to reach the necessary temperature should be kept as short as possible in order to permit a high throughput of instruments and appliances to be cleaned. Finally, the quantity of water required for the generation of steam should be kept as small as possible to save expensive water suitable for autoclaves, on the one hand, and to prolong the cycles between filling and emptying the apparatus as much as possible, on the other hand.

Finally, all this should be effected as economically as possible, i.e. the components and fittings used should be cheap products manufactured on a large scale in order to reduce the costs of production, service and maintenance.

The apparatus according to the publication mentioned above substantially satisfies the mentioned requirements, but it has turned out that it is still possible to make improvements, in particular as regards the arrangement and connection of the steam generator and the condensate collector.

In the apparatus according to the publication mentioned the steam generator, the condensate collector and the treatment chamber proper of the autoclave are connected in parallel, with a steam pipe extending from the upper section of the steam generator because of the different density of the steam and the condensate which may be connected via a three-way valve either with the condensate collector or the chamber. In an analogous manner a condensate drain extends from the chamber to a three-way valve which optionally connects it with the lower end of the condensate collector or the steam generator.

The known apparatus comprises of course additional components and connecting pipes, such as in particular a branch pipe from the condensate drain from the chamber, but these components and connections are insignificant for the present invention so that the above-mentioned publication is referred to for their understanding.

It has turned out that with the conditions and objectives mentioned at the beginning which any designer of an autoclave for medical appliances and instruments is subjected to the described construction needs relatively much space and is relatively cost-intensive in the production due to the use of two electromagnetically operated valves. In this connection it has to be borne in mind that the individual parts mentioned have to be connected with one another by pipes, that these pipes have to be connected with the individual parts by union nuts or the like so that dimensions are unavoidable here which do not conform to the aims mentioned at the beginning.

The aim of the invention is to eliminate these problems and to provide a compact, simple and reliable component which can be manufactured inexpensively and which fulfils the mentioned tasks.

According to the invention these aims are achieved by positioning the condensate collector directly above the steam generator, preferably next to the steam dome which is staggered with respect to the steam generator, by positioning a check valve between the condensate collector and the steam generator and by providing a check valve at the mouth of the feed pipe of the condensate to the condensate collector.

In this way the pipe between the condensate collector and the steam generator with all connections and intakes is completely dispensed with and the costly and interference-prone three-way valve in the condensate pipe may be dispensed with, it is replaced by the two cheap, robust and reliable check valves without resulting in any losses or disadvantages in functional respects.

The construction and mode of functioning of the device according to the invention is disclosed in greater detail by the attached drawing.

Figure 2:
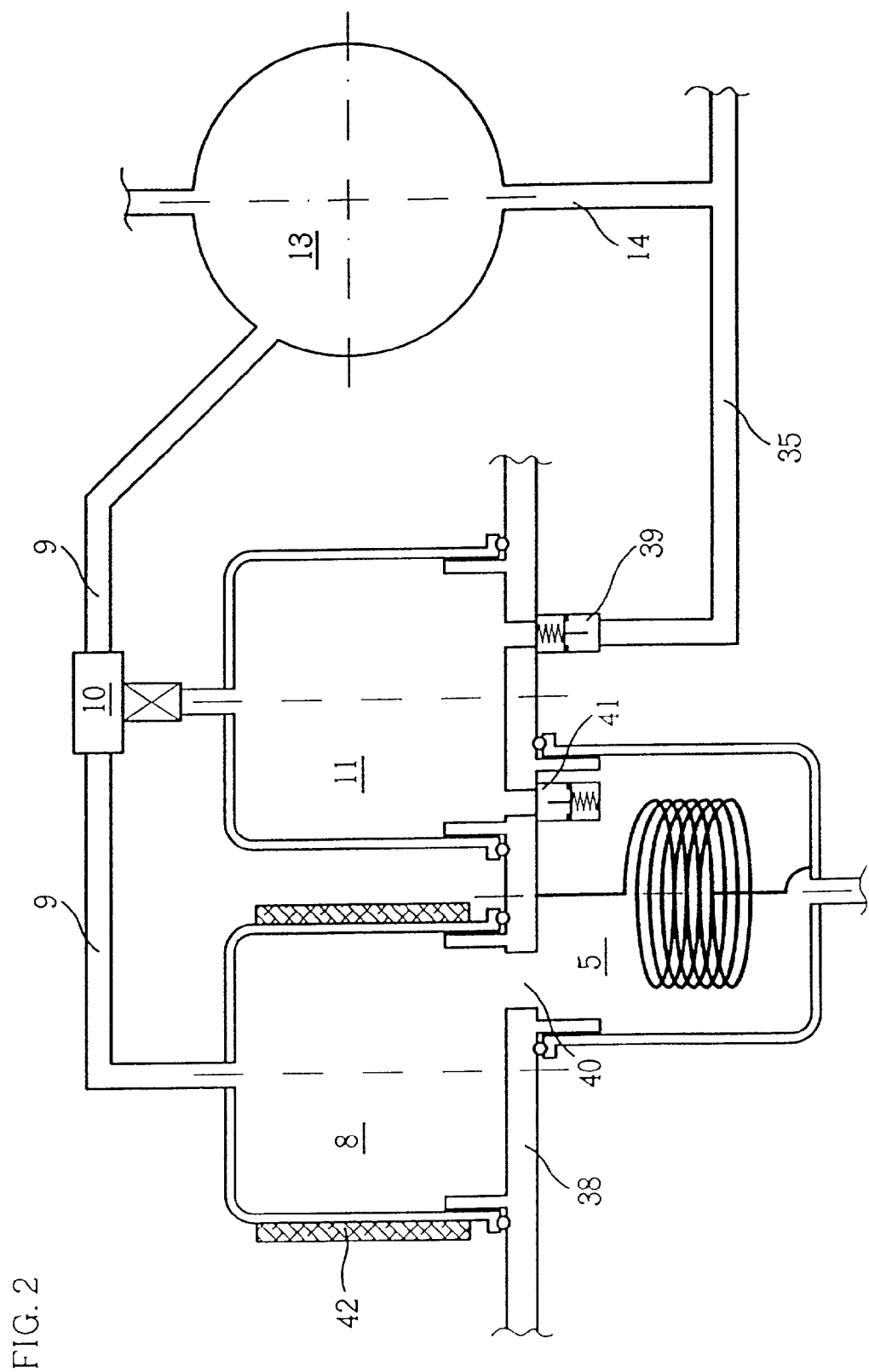

FIG. 1 shows the device according to the prior art,

FIG. 2 the construction and connection of the steam generator and the condensate collector according to the invention.

As may be seen from FIG. 1, the invention provides an autoclave with the following features:

The process water, taken from a tank 1 through a filter 2, is injected by a pump 3 in a steam generator 5. The steam generator 5 is equipped with an eccentric positioned heating element 4 and a temperature sensor 6.

A safety valve 7 is connected to the steam generator. A tube 9 links the steam dome 8 of the generator 5 to a three way valve 10 and depending on it's position, to the chamber 13 or the condensation accumulator 11.

When the three way valve 10 is switched, the steam reaches the chamber 13 and the pressure in the chamber increases. When the chamber 13 is drained, the steam streams through a one way valve 14, an embranchement 15, through a tube 34 and a drain valve 16 to a condenser 19 and is pumped off by the vacuum pump 20 into a waste tank 31.

During the pressure pulses and the sterilisation process, the drain valve 16 is kept closed and the chamber is connected to the condensation collector 11 through branching 15 to a tube 35 to another three way valve 17, its position in these phases depends on the position of the above mentioned three way valve 10. The condensation collector 11 is directly linked with the chamber but its temperature is lower. This "cold point" creates a physical phenomenon similar to a little vacuum, sucking out the condensation from the chamber 13. From here it is discharged in regular intervals into the steam generator 5 to be heated up again. This process according to the invention saves water, energy and time.

An air-inlet-valve 18 is connected to the pipe 34 downstream of the valve 15 but upstream of the condenser 19. Through this valve 18 and its pipe 36, a precisely predetermined quantity of air is added to the condenser-bound steam for two reasons: Firstly to obtain a perfect and continuous drain of the condenser and secondly to allow the membrane pump 20 to suck directly water thereby guaranteeing a low noise level.

Of course these so called "vacuum losses" are therefore determined in relation to the flow rate of the membrane pump 20 in a way to reach easily the predetermined optimal values in all the vacuum phases.

In the meantime, during the vacuum phases, it is possible to heat up the steam generator 5 in order to "accumulate" steam for the next pressure pulse. As soon as the pressure in the chamber 13 has dropped to the predetermined value, the drain valve 16 is closed and both three way valves 10 and 17 are so switched that the steam prepared in the steam generator 5 is injected into the chamber 13 and the condensation which has been formed in chamber 13 is extracted and returned through the condensation collector 11 to the steam generator 5, until predetermined pressure and temperature values are reached again in chamber 13.

Having reached this stage, new vacuum/pressure pulses can start, and so on . . .

With the successive vacuum and pressure phases it is possible to reach a residual air percentage of less than 0.1%. In a preferred embodiment, in order to reduce and optimise the duration of the air expulse procedure and the total cycle, a time out has been fixed for the first three vacuum pulses (ex: 3 min). If the vacuum pulses do not reach within this time out the predetermined value (ex: −0.80 bar), the maximum negative pressure is registered and the cycle goes on.

At the end of the three pulses, the microprocessor calculates the theoretical complementary vacuum and defines the value of the 4th additional pulse with the registered values so that the theoretical air residual percentage can be reached.

Even after the expulsion of the air by the fractionate vacuum, during the build-up of the pressure and sterilisation phases, the condensation has to be regularly drained from the chamber 13. In order to achieve this, both three way valves 10 and 17 are switched in a position which, as explained before, separates the chamber 13 completely from the steam generator 5 and leads the condensation to the condensation collector 11.

The additional advantages of this part of the invention are that the chamber 13 and especially its content, the load, remains even during the pressure pulse as dry as possible, which brings a reduction of the condensation passing through the condenser 19 and the vacuum pump 20 during the vacuum phase. All such condensation heats them up and reduces needless their efficiency, so any reduction of condensation passing through the condenser and the vacuum pump is a valuable progress.

Further, the dry state of the chamber 13 and its load improves the drying process and reduces its duration. So, the invention allows for a perfect obeyance of the well known imperative: "To get a perfect drying, avoid to moisten the load"

During the drying phase, the internal temperature of the steam generator 5 shall be reduced to about 105° C. which allows for a direct draining by opening the waste valve 21 leading to the waste tank 31 without cooling the steam.

Additionally to the described components and pipes appropriate in the described preferred embodiment of the invention, the drawing still discloses other features, elements and parts:

The chamber 13 is provided with two temperature sensors 6' and 6" in order to obtain, at each phase of the process-cycle, with sufficient reliability the temperature prevailing in the chamber. For checking and surveillance purposes, connections 22 for a pressure test and 23 for a temperature test can be used. The chamber 13, having a thermal insulation, is heated by an external heating element 12, which temperature is controlled by an external sensor 24 completely independently from the internal ones.

In order to introduce external sterile air, the chamber 13 is connected to an air inlet by a tube 25, through a valve 28, a one way valve 27 and a bacteriological filter 26. It is necessary, at the end of the sterilisation process, to equilibrate the chamber to the atmospheric pressure prior to the opening of the door.

To empty the tanks 1 and 31, drain cocks are foreseen respectively 29 for the pure water, and 29' for the waste. Additionally, a connection to an external pure water tank is provided in a way to have an automatic refilling of the pure water tank 1 by a water pump 30. Both tanks 1 and 31 are most completely watertight and need external connections 32 and 32'.

The tanks are equipped with water level sensors 33, 33' and 33", in order to prevent under-or overfilling. The condenser 19 is air cooled but a water cooled condenser can be used without altering the generic concept of the invention or leaving its scope. The represented membrane pump 20 can be replaced by any other pump used for such application.

In the drawing, the pipes are shown in a purely schematic manner, it is clear for the man skilled in the art that various details, which are not part of the invention have to be taken into account. The position of the parts relative to each other, the necessity to use further pumps or different heights of the parts in order to provoke a natural circulation and all mechanical features have no room on a fluid diagram which the drawing is.

Similarly, all kind of materials and the electronic control means have not been discussed, because it is clear for the man skilled in the art that the materials and the electronics usually used in connection with autoclaves can be used for the invention too.

Naturally, it is preferred to have a full-automatic autoclave which only has to be loaded and unloaded and detects all kind of failures by itself, stops its functioning and gives the pertinent messages, but it is clear that a "manual handling" is possible too.

FIG. 2 shows a diagrammatic view of the section of an autoclave according to FIG. 1 which is directly affected by the invention. In the preferred embodiment as shown in FIG. 2 the condensate collector 11, the steam generator 5 and the steam dome 8 each have the shape of a pot and are tightly mounted with the open side on a common mounting plate 38, e.g. by means of a flange (not shown) and appropriate screws with an intermediate seal, preferably an O-ring seal.

In the preferred embodiment shown by FIG. 2, the condensate pipe 35 extending from the autoclave chamber 13 ends in the mounting plate 38, a check valve 39 preventing the condensate or steam from flowing back from the condensate collector 11 into the pipe 35 being positioned either in the mounting plate or at the end of the pipe. Preferably, a filter is mounted in the pipe 35 before the check valve 39 in order to protect the valve from all kind of impurities. The filter may be of any known type or kind, plastics material with a medium pore diameter of about 0.5 mm is preferred.

As shown by FIG. 2, the condensate collector 11 and the steam dome 8 are mounted on one side of the mounting plate 38 in such a manner that in the direction perpendicular to the mounting plate 38 their cross-sections each partly cover the cross-section of the steam generator 5. Thus the steam generator 5 may be connected with the steam dome 8 to form a functional unit by a simple opening 40 in the mounting plate 38, while the connection between the condensate collector 11 and the steam generator 5 is effected by an opening in the mounting plate 38 which carries a check valve 41 which prevents any medium flowing from the steam generator 5 to the condensate collector 11.

For clarity's sake, the individual sensors, safety valves and the like, as partly shown in FIG. 1, have no longer been inserted in FIG. 2, these and other components necessary for the operation of an autoclave or increasing its operating convenience are well-known to the expert in the field of autoclave construction and need not be discussed in connection with the present invention.

The mode of functioning of the device according to the invention is as follows: When the three-way valve 10 connects the condensate collector 11 with the autoclave chamber 13 and when at the same time the steam generator 5 is activated for the next steam injection phase, the condensate collector 11 acts as a cold sack in which the condensate collects which is generated during the continuous cooling of the entire system 11, 13. This condensate may get from the chamber 13 through the pipe 35 and the check valve opening in this direction or the one-way valve 39, respectively, into the condensate collector 11. At the same time condensation may take place through the pipe 9 and through the valve 10.

In the following the three-way valve 10 is changed so as to connect the steam dome 8 with the autoclave chamber 13 which increases the pressure in the entire system, thus also in the condensate collector, and the pressure required by various standards and the desired temperature are reached in the chamber 13 and maintained for a predetermined period of time. After expiration of that period of time the steam generator 5 is deactivated and as a result of cooling and pressure loss the condensate collected in the condensate collector 11 flows to the steam generator 5 where it is ready for the next heating cycle for the next steam injection.

In this way the electromagnetically operated three-way valve 17 necessary according to the prior art may in fact be dispensed with, and by dispensing with the individual pipes between the discretely constructed components the apparatus may be designed substantially more compact than so far.

According to a preferred embodiment of the invention the condensate collector 11, the steam generator 5 and the steam dome 8 consist of interchangeable pot-like containers each so that it is not necessary to built and assemble (and keep on stock for repairs) three different parts, but one component may be used for each of the three purposes as required. As is shown by the purely diagrammatic view of FIG. 2, each of the components requires a connection for a pipe in the central bottom area; in the steam generator 5 this is a drain pipe for emptying the apparatus, in the steam dome 8 the steam pipe 9 which leads to the autoclave chamber 13 via the three-way valve 10, and in the condensate collector 11 the connection with the three-way valve 10.

If the application of fitting or sensors, e.g. in the area of the steam dome 8, is desired, an appropriate opening with connecting fitting may of course be provided at the appropriate place in the casing of the top-like vessels; if used as a steam generator 5 it may serve e.g. as a level meter and if used as a condensate collector 11 as a level meter or as a temperature sensor, or may also be closed with a stopper.

In FIG. 2 a thermal insulation 42 is indicated in the area of the steam dome 8 which may of course also extend to the cover of the steam dome 8 and the pipe 9; the indication in the figure is merely illustrative.

The vessels 5, 8 and 11 and the mounting plate 38 may be made of special steel (austenitic stainless steel) or another material permitted in medical apparatus, among others in particular high-strength plastic materials which are increasingly used in medical apparatus. These materials are known to the expert in the field of autoclave construction, they are the same as usually used in the discrete design of an autoclave.

Further changes and adaptations in regard to the described and shown embodiment consist in waiving the steam dome 8 and connecting the upper part of the steam generator directly with the chamber 13. Especially in this case, the heating element 5 may be substituted by an heating which extends around the steam generator which then is preferably heavily insulated. It is possible in this case to provide a superheating to the steam by a further heating element at the beginning of the steam pipe 9 in or near the upper part of the steam generator.

The invention claimed is:

1. An autoclave for medical appliances and instruments, comprising:
    a chamber (13) in which the appliances to be sterilized are located;
    a steam generator (5) connected with the chamber (13) by a steam pipe (9),
    a feed pipe (35) for discharging condensate from said chamber (13) into the steam generator through a condensate collector (11);
    a water tank (1) arranged to supply process water to the generator (5),
    the condensate collector (11) being positioned above and in tight connection with the steam generator (5) and along the feed pipe (35), between the chamber (13) and the steam generator (5), the condensate collector being pressurizable and distinct from the water tank (1) and directly linked with the chamber (13);
    a first check valve (39) at the mouth of the feed pipe (35) to the condensate collector (11) so as to prevent the condensate from flowing back from the condensate collector (11) into the pipe (35);
    and a second check valve (41) between the collector (11) and the steam generator (5) so as to prevent any medium from flowing to the condensate collector (11) from the generator (5), wherein the condensate collector (11) and the steam generator (5) consist of pot-like vessels each having an open side which are tightly mounted with their open side on a common mounting plate (38), the mouth of the feed pipe (35) and a connection opening between the collector (11) and the generator (5) being provided in the common plate.

2. The autoclave as in claim 1, and further comprising a three-way valve (10) arranged so as to separate the steam generator from the chamber (13) and connect the collector (11) to the chamber (13).

3. The autoclave as in claim 1, and further comprising a steam dome (8) provided above and staggered with respect to the steam generator (5).

4. The autoclave as in claim 3, wherein the steam dome consists of a pot-like vessel and is mounted on the common plate (38) on the same side as the condensate collector (11).

5. The autoclave as in claim 1, wherein the pot-like vessels are all identical and interchangeable.

6. The autoclave as in claim 1, wherein the pot-like vessels are all identical and interchangeable.

* * * * *